United States Patent [19]
Shippert

[11] Patent Number: 5,947,123
[45] Date of Patent: Sep. 7, 1999

[54] NOSE SPLINT WITH CONTOURED NOSE CONTACTING SURFACE

[76] Inventor: Ronald D. Shippert, 4975 S. Albion St., Littleton, Colo. 80121

[21] Appl. No.: 09/041,044

[22] Filed: Mar. 6, 1998

[51] Int. Cl.[6] .............................. A61F 9/00; A61F 13/00; A61F 5/08
[52] U.S. Cl. ...................... 128/858; 602/41; 606/204.45
[58] Field of Search .............................. 606/204.45, 199, 606/191, 196; 602/6, 17, 74, 902, 53, 58, 41, 47; 623/10; 128/848, 858, 857, 204.12, 206.18, 200.24, 206.11, 206.14, 206.25

[56] References Cited

U.S. PATENT DOCUMENTS

| | | | |
|---|---|---|---|
| 4,005,709 | 2/1977 | Laerdal | 602/53 |
| 4,140,115 | 2/1979 | Schonfeld | 602/54 |
| 4,153,051 | 5/1979 | Shippert . | |
| 4,213,452 | 7/1980 | Shippert . | |
| 4,274,402 | 6/1981 | Shippert . | |
| 4,377,159 | 3/1983 | Hansen | 602/53 |
| 5,022,389 | 6/1991 | Brennan | 128/858 X |
| 5,611,334 | 3/1997 | Muchin | 128/848 X |
| 5,653,224 | 8/1997 | Johnson | 128/858 X |
| 5,690,610 | 11/1997 | Ito et al. | 602/53 |
| 5,711,026 | 1/1998 | Kaltman et al. | 128/200.24 |
| 5,755,232 | 5/1998 | Kalt | 128/845 |
| 5,806,525 | 9/1998 | Pope, Jr. | 128/848 |

*Primary Examiner*—Richard J. Apley
*Assistant Examiner*—Densie Pothier
*Attorney, Agent, or Firm*—Sheridan Ross P.C.

[57] ABSTRACT

A nose splint is disclosed that adhesively adheres to a patient's nose. The nose splint is formed in an area on and around the nose by molding the splint to the contour of the patient's nose, thereby pressing any edema fluid between the incised skin, and the bone and cartilage out of this area so that the skin tightly engages the bone and cartilage during healing. The nose splint has a novel shaped central pad member that fits along the ridge of the nose. The shape of the pad allows the adjacent overlapping portions of the nose splint to smoothly fold about the patient's nose forming a smooth composite surface that reduces wrinkling of the skin on the patient's nose and reducing voids where the adhesive does not adhere to the patient's skin.

17 Claims, 4 Drawing Sheets

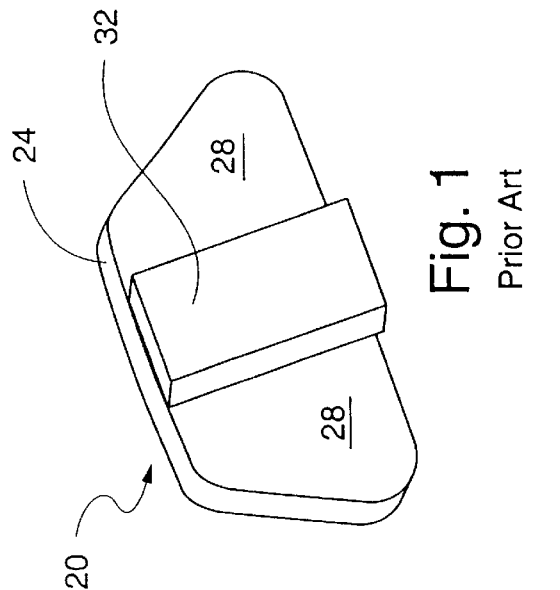
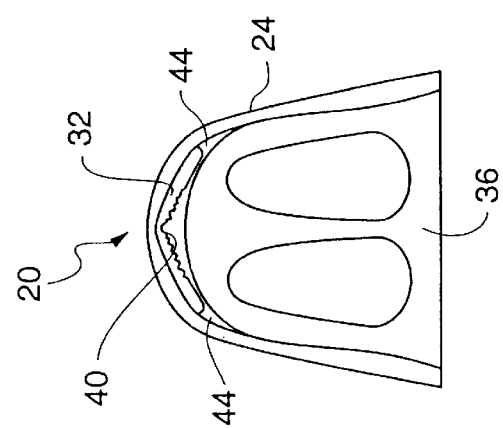
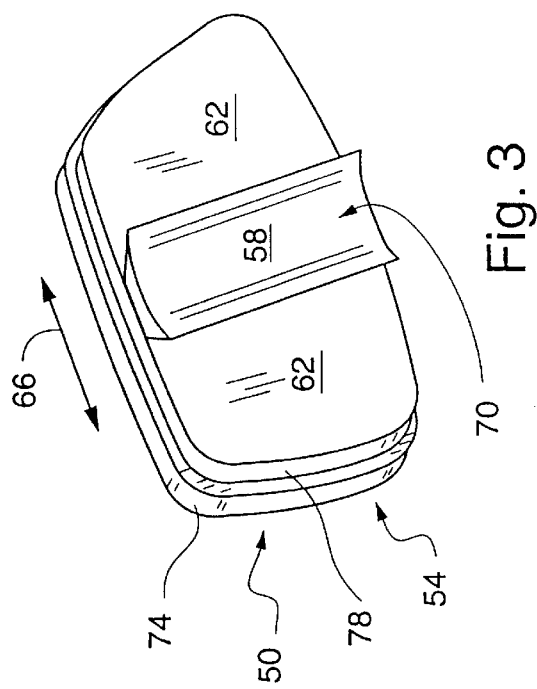

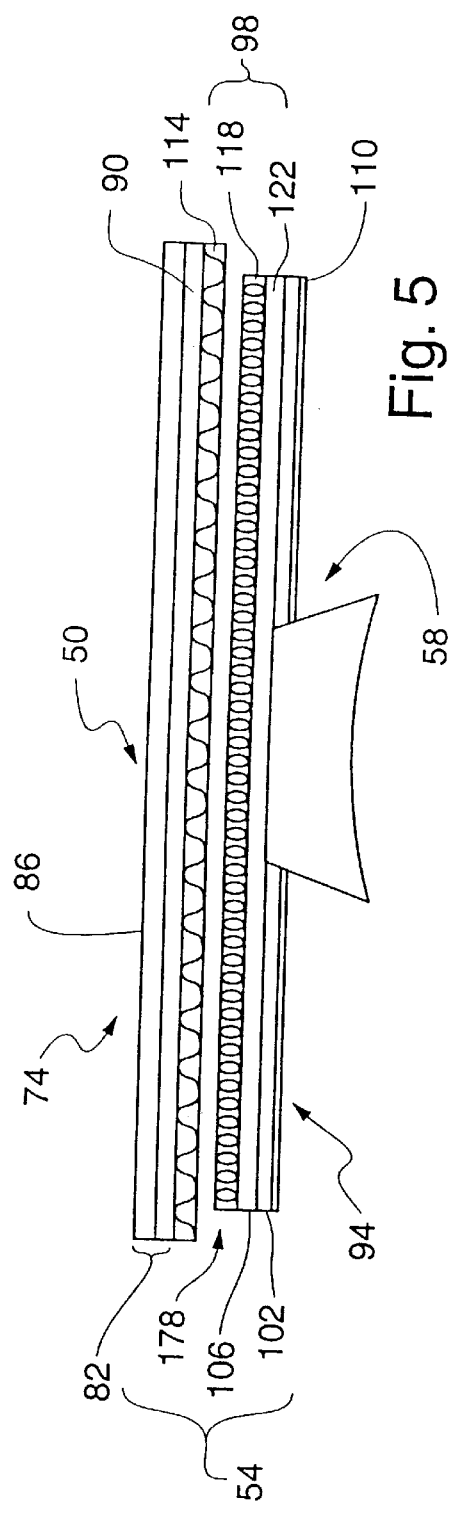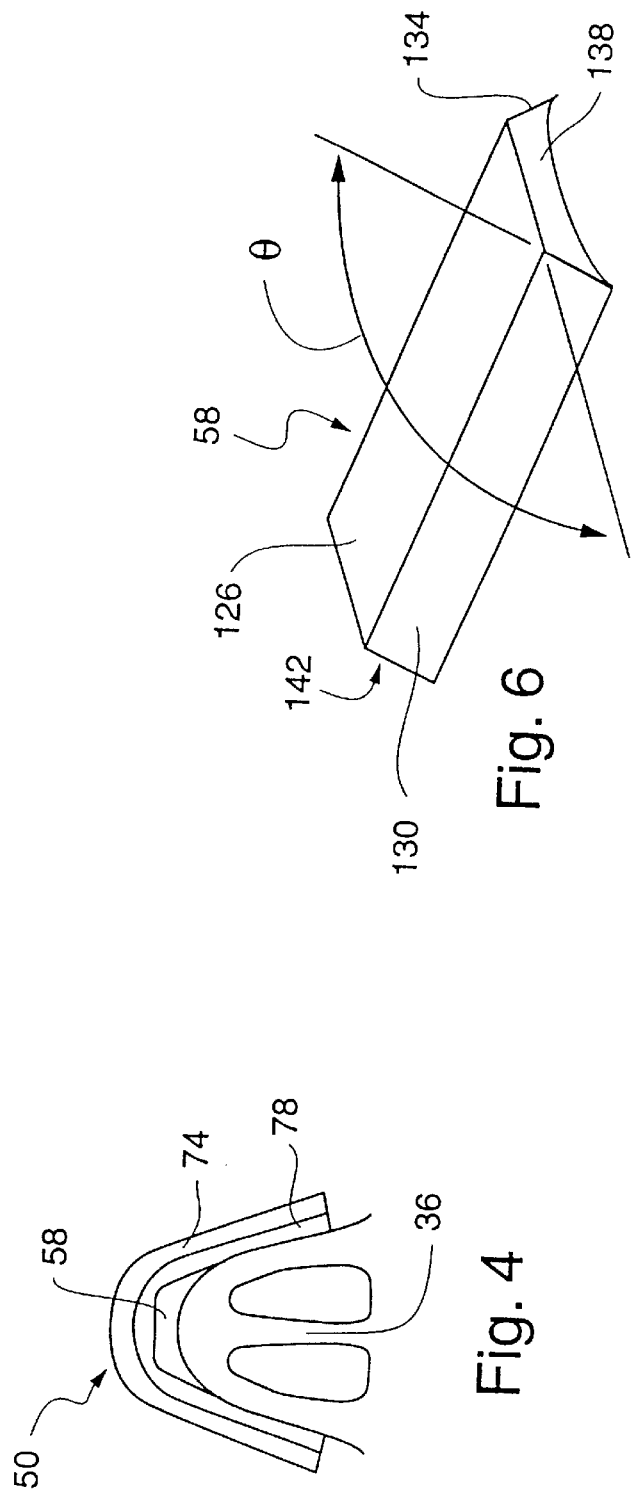

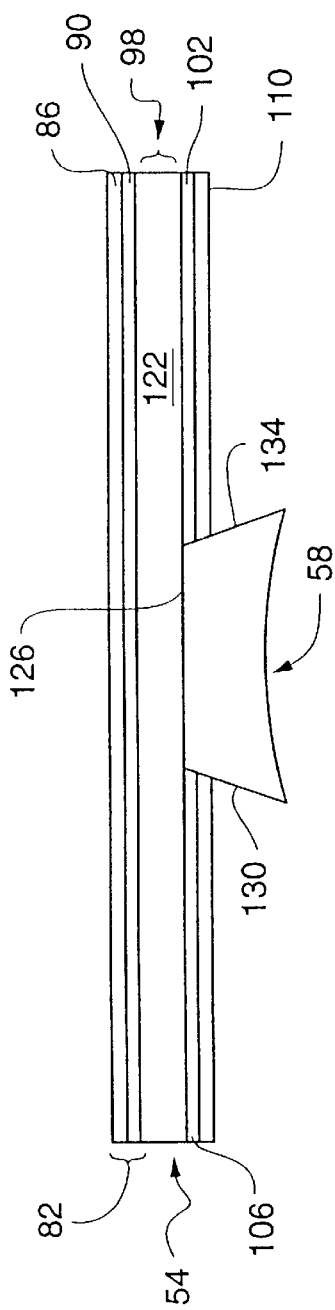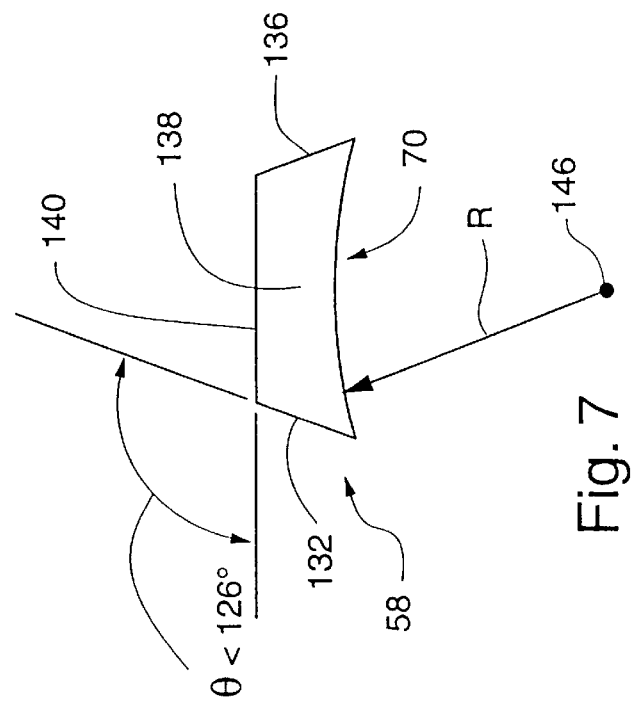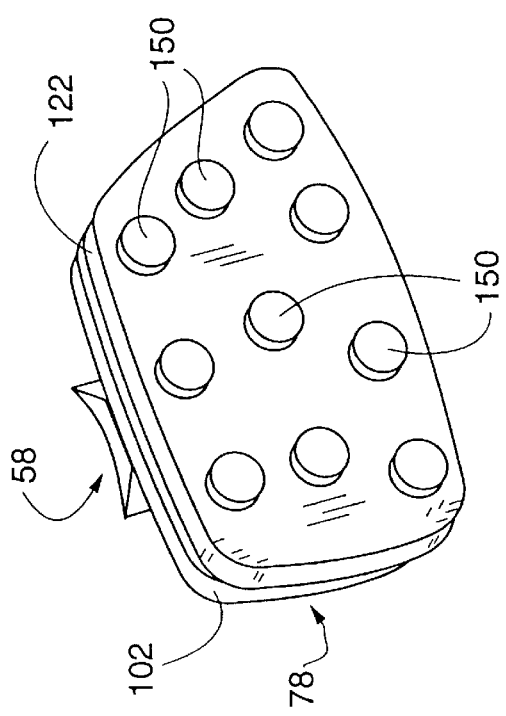

NOSE SPLINT WITH CONTOURED NOSE CONTACTING SURFACE

FIELD OF THE INVENTION

The present invention relates to nose splints, and in particular, to nose splints having nose contacting surfaces that smoothly conform to a patient's nose.

BACKGROUND OF THE INVENTION

Various techniques have been developed for use in maintaining facial bones in place after, for example, surgery. Such nose splints are primarily designed to maintain constant pressure on precise areas of the nose to prevent swelling or distortion thereof that can potentially cause abnormal healing of the nose. Accordingly, various types of nose splints have been developed such as plaster molded nose splints, and nose splints integrated into facial masks. Further, nose splints have been developed that include a malleable but firm material such as a soft metal that can be conformed to a patient's nose and attached to the patient's nose and surrounding tissue by adhesives of various types. This latter type of nose splint has advantages over the former types in ease of application and aesthetic appearance. However, when such a nose splint is contoured to a patient's nose, the inner surfaces of the splint that contact the patient's nose can fold or crease in unwanted or inappropriate ways. Such folding or creasing can distort the skin of the patient's nose (if the adhesive is sufficiently strong to pull the skin and tissue into the folds or creases generated by the bending of the splint about the nose), or the folds and creases of the nose contacting portions of the nose splint might not sufficiently adhere to the patient's nose and thereby allow the splint to more easily detach from the patient unexpectedly.

An example of a malleable adhesively-applied nose splint in the prior art is shown in FIGS. 1 and 2. In FIG. 1, such a nose splint 20 is shown in a configuration prior to application to a patient's nose. The nose splint 20 includes a layered splinting panel 24 that at least includes a layer of malleable yet relatively firm material, such as aluminum, and a layer of resilient material such as a foam and/or a polymer material. Further, the surface 28 of the panel 24 may have an adhesive coating thereon for attaching to the skin on and about the patient's nose. Additionally, the nose splint 20 may also include a nose pad 32 that is intended to extend along the ridge of the nose as shown in FIG. 2. Note that the nose pad 32 has a relatively simple geometric configuration, wherein the surfaces of the nose pad meet at right angles to one another.

As shown in FIG. 2, when the nose splint 20 is applied to patient's nose 36, the nose pad 32 cannot easily conform to the curvature of the patient's nose due to the geometry of the nose pad. As FIG. 2 illustrates, the nose pad may have one or more creases 40 since the pad does not have a configuration that allows or compensates for the bending of the panel 24 about the patient's nose so that a smooth contoured surface is provided along the ridge of the patient's nose. Further, in addition to the creases 40, voids 44 are created wherein the panel 24 is not adhesively attached to the patient's nose. The adjacent portions of the nose pad 32 adjacent to such voids may be excessively compressed against the patient's nose in comparison to other portions of the nose pad 32 when the substantially block-like nose pad 32 is forced to conform to the arcuate ridge of a patient's nose. Thus, this excessive pressure adjacent to the voids 44 has a tendency to crinkle the patient's skin into the creases 40 and can cause the voids 44 to increase over time as the adhesive on the surface 28 of the panel 24 weakens. Thus, it would be advantageous to have a nose splint that reduced or prevented the creases 40 (and voids 44), and the associated wrinkling of the patient's nasal tissue into such creases. Further, it would be advantageous to have a nose splint where the pressure of the nose splint along the ridge of the nose is substantially uniform.

SUMMARY OF THE INVENTION

The present invention is a nose splint having preformed contoured surfaces for contacting a patient's nose and surrounding tissue in a manner that provides a smooth, continuous skin contacting composite surface for reducing creases that can cause wrinkling of the skin underneath the nose splint. More particularly, the nose splint of the present invention has an adhesive layer on the contoured composite surface so that the nose splint can adhere to the patient's nose and surrounding tissue. The contour of the composite surface for contacting the patient is such that when the contoured composite surface is molded about the shape of the patient's nose the contoured composite surface forms a sufficiently smooth surface. Consequently, there are substantially no creases in the composite surface wherein the patient's skin could be fixed into an unsightly crease pattern by the crowding of the tissue. Moreover, since such a smooth contour of the composite surface also assures that a greater amount of the adhesive layer contacts the patient's skin, the nose splint of the present invention tends to stay in position for a longer time than nose splints having non-contoured patient contacting surfaces.

The smooth patient contacting composite surface of the present nose splint is substantially provided by a novel geometrically shaped resilient pad that is intended to be placed along the ridge of the patient's nose. This pad has an arcuate surface for contacting the patient's nose and angled sides to this arcuate surface such that the angled sides extend, generally, in the direction of the contour of the patient's nose where the angled sides meet the patient's nose. More particularly, the novelly shaped pad has an across-the-nose cross-section that is generally in the shape of a trapezoid, wherein the arcuate surface forms the base of the trapezoid. Thus, in one embodiment, the top or opposed trapezoidal face (i.e. opposed to the trapezoidal base) of the pad is where the pad is bound to the preformed planar (and adhesive coated) inner surface of the nose splint that contacts the patient. Accordingly, the trapezoidal sides of the pad flare out away from this inner surface at an angle of less than 90° and more preferably in the range of 54° to 80°. Alternatively, the degree of flaring can be measured in terms of the complementary angle (between the top face of the pad and a side of the pad), wherein this complementary angle is greater than 90° and more preferably in the range of 100° to 126°.

In addition to the above aspects of the present invention, various embodiments can also include predetermined air channels within the nose splint so that a greater volume of air can circulate within or through the nose splint to thereby dissipate perspiration buildups underneath the nose splint which can cause the nose splint to detach prematurely.

Other features and benefits of the invention will become apparent from the detailed description with the accompanying drawings contained herein.

BRIEF DESCRIPTION OF THE DRAWINGS

FIG. 1 shows a prior nose splint 20 that can be bent or molded around a patient's nose.

FIG. 2 illustrates the problems encountered when bending or molding the prior art nose splint 20 about a patient's nose, wherein creases 40 and voids 44 occur.

FIG. 3 shows a perspective view of an embodiment of the present invention, wherein a novelly geometrically shaped pad member 58 is provided on a mid-portion of a substantially planar layered splinting panel 54 having separable subpanels 74 and 78.

FIG. 4 shows the nose splint 50 of the present invention formed about a patient's nose 36.

FIG. 5 shows an end view of the embodiment of the nose splint 50 that is also shown in FIGS. 3 and 4.

FIG. 6 shows a perspective view of the pad member 58.

FIG. 7 shows an end view of the pad member 58.

FIG. 8 shows an interior layer of the layered splinting panel 54, wherein this layer is provided by a plurality of patches of loop material for mating with a layer of hook material (not shown in this figure).

FIG. 9 shows an end-on view of an alternative embodiment of the present invention, wherein the layered splinting panel 54 is of unitary construction having a foam layer as its inner layer.

DETAILED DESCRIPTION OF THE PREFERRED EMBODIMENT

Figure 11:
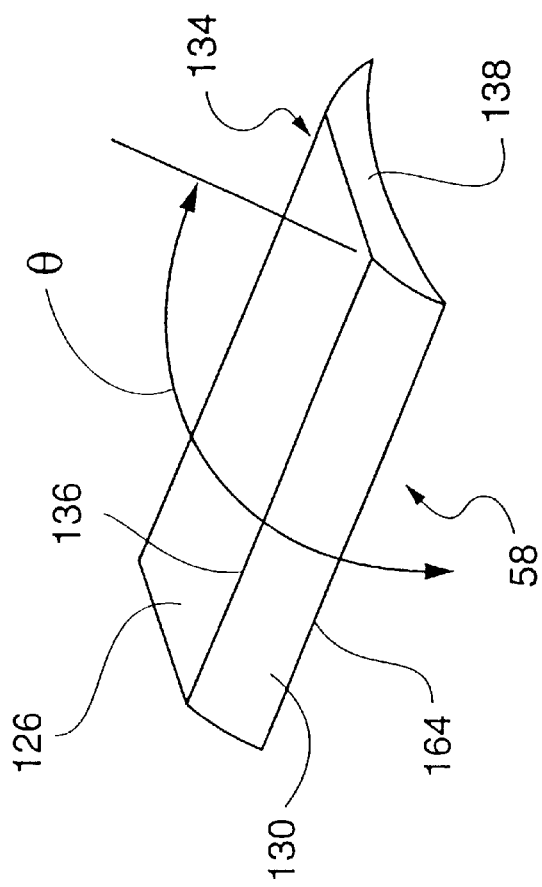
FIG. 11 shows a perspective view of an alternative embodiment of the pad member 58.

FIG. 3 illustrates an embodiment of a nose splint 50 according to the present invention. The nose splint 50 includes a layered splinting panel 54 which includes a plurality of layers as will be discussed in detail with reference to FIG. 5. Additionally, the nose splint 50 includes a pad member 58 of resilient material such as a polyurethane foam or other polymeric material. Further note, as will be discussed in detail below, the pad member 58 has a geometrical configuration that is substantially different from the nose pad 32 illustrated in the prior art FIGS. 1 and 2. In particular, the pad member 58 flares out from the surface 62 so that the width of the pad member along the directions of the double-headed arrow 66 increase as the offset from the plane of the surface 62 increases. Additionally, note that the pad member 58 has a curved nose-contacting surface 70 (also denoted hereinafter as the "bottom side" of the nose pad) for more nearly conforming to a curvature of the ridge of a patient's nose as will be discussed in further detail hereinbelow. Further note that the panel 54 may have two separable subpanels (each subpanel having one or more layers) that are attached together by, e.g., hook and loop materials, and that the subpanels may be sized differently. For example, referring to the separable subpanels 74 and 78 of FIG. 3, the separable exterior subpanel 74 is wider (along the directions of double-headed arrow 66) than the interior subpanel 78. Note that this aspect of the present invention allows a better mating of the boundaries of the two subpanels when fitted about the curvature of a patient's nose. That is, since it is preferred that the exterior panel 74 entirely cover the interior subpanel 78, the exterior subpanel must be somewhat wider for there to be a matching of the borders of the two subpanels when fitted about a patient's nose.

In FIG. 5, an end-on view of the nose splint 50 is shown, wherein greater detail of the individual layers within the layered splinting panel 54 is shown. Note that the present figure shows an embodiment of the layered splinting panel 54 that has separable subpanels 74 and 78 as in FIG. 3. However, it is within the scope of the present invention to also include panels 54 that are not readily separable into subpanels, but instead, the panel 54 is intended to be used as a unitary portion of the splint 50.

In general, nose splints according to the present invention (such as the embodiment shown in FIG. 5) include an outer layer 82 having an external paint/plastic sublayer 86 that is fixedly attached to a malleable splinting sublayer 90, wherein the sublayer 90 provides the required rigidity and shape-holding characteristics of the nose splint 50 when the nose splint 50 is formed about the patient's nose 36. In particular, this splinting layer 90 may be of a soft metal such as aluminum of a sufficient gauge for withstanding any shape-distorting pressures induced by, e.g., swelling on or about the patient's nose. Accordingly, the outer layer 82 is both malleable and sufficiently rigid once conformed to the patient's nose to provide the shape-retaining structure of the splint 50. Note that the remaining portions of the nose splint 50 are hereinafter also referred to as the support assembly 94. Thus, in the embodiment of the nose splint 50 of FIG. 5, the support assembly 94 includes an inner layer 98 (itself having a plurality of sublayers), an adhesive layer 102 attached to an inner surface 106 of the inner layer 98, wherein the adhesive layer is used to secure the nose splint 50 to the skin of the patient's nose. Further, the support assembly 94 includes a removable backing member 110 that covers the adhesive layer 102 and thereby protects this adhesive layer until such time that the removable backing member is removed and the adhesive layer 102 is pressed against the patient's nose 36. Also included in the support assembly 94 is the pad member 58 which is attached to the inner surface 106 of the inner layer 98 substantially in a mid-portion of the inner layer 98; i.e., having symmetric portions of the inner layer 98 disposed about the pad member 58. Note that this inner surface 106 is straight, continuous, and forms a substantially planar surface prior to being formed about a patient's nose. Further note that at the juncture of the pad member 58 and the inner surface 106, there is a discontinuity in that, e.g., the juncture of the side surface 130 (described further hereinbelow) and the inner surface 106 defines an abrupt change in curvature when moving from one of these surfaces to the other of these surfaces. In fact, when traversing the inner surface 106 from the edge of the subpanel 78 toward the pad member 58 along a direction of arrow 66, the transition to the side surface 130 is both abrupt in the curvature change and additionally, reverses the direction of traversal in the direction of arrow 66.

FIG. 4 shows the nose splint 50 of FIG. 3 as it appears when formed about the contours of a patient's nose 36. In particular, note that, due to the geometrical shape of the pad member 58, the interior nose-contacting composite surface of the nose splint 50 provide a substantially smooth, continuous and non-creased contact area with the patient's nose 36. That is, the creases 40 and the voids 44 shown in FIG. 2 are substantially eliminated when the nose splint of the present invention is applied to a patient's nose.

Referring again to the nose splint 50 embodiment of FIG. 5, the inner layer 98 includes a sublayer of hook material 114 that is intended to mate with an adjacent sublayer of loop material 118 for thereby securing together the separable exterior subpanel 74 and the interior subpanel 78. The sublayer of loop material 118 is fixedly attached to a sublayer of foam material 122. Accordingly, the adhesive layer 102 and the pad member 58 are provided on the inner surface 106 of the foam material 122.

FIGS. 6 and 7 illustrate in greater detail the geometrical configuration of the pad member 58. Accordingly, the external surfaces of the pad member 58 can be described as follows:

(a) a top surface 126 that is attached to the inner surface 106 when the nose splint 50 is fully assembled.

(b) first and second side surfaces 130 and 134 respectively, wherein the first (second) side surface 130 (134) intersects the plane of the top surface in a first (second) side edge 132 (136) at an angle $\theta$, wherein $\theta$ is greater than 90° and more preferably in the range of greater than or equal to 100° but less than 126°.

(c) first and second ends 138 and 142 respectively, which are in the present embodiment planar and intersect the top surface 126 and first and second sides 130 and 134 at right angles. In particular, the first end 138 intersects the top surface 126 along top edge 140, wherein the angle $\theta$ is the outside angle between, e.g., the first side edge 132 and the top edge 140.

(d) a bottom surface, also previously denoted as the nose-contacting surface 70, wherein this surface is curved substantially conforming to a surface of a cylinder having a central axis normal to the first end 138 and including the point 146 (FIG. 7). Moreover, note that the radius R indicating the distance from the point 146 to the bottom surface 70 is approximately 14.02 mm±20%. Further, note that the width of the bottom surface 70 along the directions of the double-headed arrow 66 (FIG. 3) is approximately 6.35 mm±20% whereas the width of the top surface 126 in the same directions is approximately 3.68 mm±20%.

Various other embodiments of the nose splint 50 are also within the scope of the present invention. In particular, regarding FIG. 8, an alternative embodiment of the subpanel 78 is shown, wherein instead of having a continuous sublayer of loop material 118 (as in FIG. 5), the loop material is instead dispersed upon the surface of the sublayer of foam material 122 so as to provide air spaces between the Velcro portions 150 attached to the sub-layer of foam material 122. Note that such air spaces may be beneficial to the nose splint 50 in that a cause of such nose splints undesirably detaching from the patient's nose is due to excessive build-ups of perspiration between the adhesive layer 102 and the skin on and about the patient's nose 36. Accordingly, by providing additional ventilation whereby moisture from such perspiration can escape through the interior subpanel 78 more readily, it is believed that the nose splint 50 will adhere to the patient's nose 36 for a longer period of time than in other embodiments where such air spaces are not provided.

In FIG. 9, an alternative embodiment of the nose splint 50 is provided, wherein the layered splinting panel 54 is of unitary construction and therefore does not have separable subpanels. Further, note that, as with the embodiments of the nose splint 50 shown in FIGS. 3, 4, 5, and 8, the pad member 58 is fixedly attached to a mid-portion of the sublayer of foam material 122 in a center portion of the panel 54 so that there is substantially an equal extent of the panel 54 extending beyond the joining of the pad member to the panel 54. More specifically, the pad member 58 is positioned on the panel 54 so that when the nose splint 50 is applied to a patient's nose, with the nose-contacting surface 70 substantially along the ridge of the patient's nose, as in FIG. 4, there are equal extents of the panel 54 on either side of the patient's nose, as, e.g., shown in FIG. 4. Note that as in the nose splint embodiment of FIGS. 3, 4 and 5, the joining of the pad member 58 to the inner surface 106 defines an abrupt change or discontinuity at the juncture of the top surface and the inner surface 106. That is, using the first side 130 and the inner surface 106 as exemplary, the first side extends away from the inner surface 106 and also overhangs a portion of the surface 106 to which the pad member 58 is not attached. Accordingly, this overhang is important in that it allows the panel 54 to fold smoothly onto the side 130 (as well as the side 134) since the first and second sides are symmetric (and extend smoothly substantially without any voids 44 onto the patient's nose 36).

Figure 10:
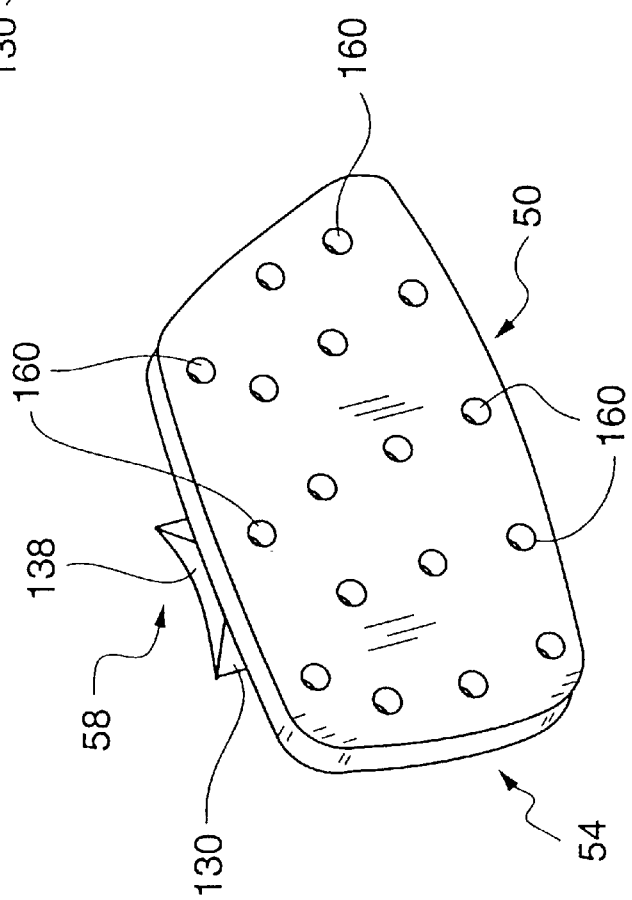
FIG. 10 shows a perspective view of another embodiment of the present invention, wherein there are holes 160 provided through the thickness of the layered splinting panel 54 to expedite the removal of perspiration from the surface of the patient's nose beneath the nose splint 50.

FIGS. 10 and 11 illustrate various additional aspects of alternative embodiments of the nose splint 50. In particular, referring to FIG. 10, the layered splinting panel 54 may have holes 160 that pierce the thickness of the panel 54 and thereby expedite the removal of perspiration from the surface of the patient's nose so that the splint 50 can adhere to the patient's nose for a longer period of time. Such holes can also be provided in the other embodiments, such as that illustrated in FIG. 5, with the holes being formed on the inner surface of the layer that is next to the patient's skin. Further note that the pad member 58 of these figures has curved sides 130 and 134. However, assuming the curvatures of the sides 130 and 134 are such that they substantially provide a smooth transition onto the patient's nose (e.g., a smooth transition between the edge 164 and the patient's nose 36) so that when the panel 54 is folded onto the sides 130 and 134, there is a substantially smooth continuous composite surface to which the adhesive layer 102 can adhere substantially without voids 44. Accordingly, it is believed that such substantially smooth transitions will be provided as long as the angle $\theta$ between a plane having the edges 136 and 164 and a plane including the top surface 126 have an angle $\theta$ therebetween that is greater than 90° and more preferably equal to or greater than 100°.

Additionally note that other geometrical configurations for the pad member 58 are also within the scope of the present invention. In general, the primary requirements for the configuration of the pad member 58 according to the present invention is that the first and second sides 130 and 134 (or the surfaces corresponding to these sides for joining the top surface 126 to the nose-contacting surface 70) provide an overhang of the panel 54 so that the panel can fold smoothly onto the first and second sides and continue substantially smoothly onto the skin on and about the patient's nose. Note that in one embodiment of the present invention, the pad member 58 need not be fixedly attached to the panel 54 prior to configuring the nose splint 50 upon a patient's nose 36. That is, the nose-contacting surface 70 of the pad member 58 may be provided with an adhesive coating on at least the nose-contacting surface 70 for thereby placing the pad member 58 onto the ridge of the patient's nose separately and prior to providing the layered splinting panel 54 over the pad member 58 and each side of the patient's nose. Accordingly, in this embodiment of the present invention, the adhesive layer 102 may extend continuously over the inner surface 106 and/or an adhesive layer may be provided on the top surface 126 of the pad member 58.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiments described hereinabove are further intended to explain the best mode presently known of practicing the invention, and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A nose splint, comprising:
   an outer layer having a length that is malleable for conforming to an outer shape of the nose; and
   a support assembly attached to said outer layer and also attachable to the nose, said support assembly including:
      an inner layer having a mid-portion; and
      a pad member separate from but attached to said mid-portion of said inner layer, said pad member including a top surface having a width and attached to said inner layer, a concave bottom surface having a width and configured to the outer shape of the nose, first and second sides and first and second ends, with said bottom surface width being greater than said top surface width;
   wherein said top surface has a first top edge and said first side has a first side edge, both being adjacent to said first end, and in which a first outside angle is defined by a first line extending through and away from said top edge and a second line extending through said first side edge, with said outside angle being greater than 90° and in which said curved bottom surface is exposed but, when said support assembly is attached to the nose, the curved bottom surface is closer to the nose than said top surface.

2. A nose splint, as claimed in claim 1, wherein:
   said inner layer has an inner surface that is straight and continuous and said top surface of said pad member is attached at said inner surface and a discontinuity is defined at the juncture of said first side and said inner surface.

3. A nose splint, as claimed in claim 1, wherein:
   said inner layer includes a foam material.

4. A nose splint, as claimed in claim 1, wherein:
   said inner layer includes separable first and second fabric materials having first and second faces, respectively, with one of said first and second faces including a plurality of hooks and the other of said first and second faces having a plurality of loops for engagement with said hooks.

5. A nose splint, as claimed in claim 1, wherein:
   said support assembly includes an adhesive layer joined to an inner surface of said inner layer and a removable backing member joined to said adhesive layer.

6. A nose splint, comprising:
   an outer layer that is malleable for conforming to an outer shape of the nose; and
   a support assembly attached to said outer layer and also attachable to the nose, said support assembly including:
      an inner layer having a mid-portion; and
      a pad member separate from but attached to said mid-portion of said inner layer, said pad member including a top surface, a bottom surface, first and second sides and first and second ends;
   wherein said top surface has a first top edge and said first side has a first side edge, both being adjacent to said first end, and in which a first outside angle is defined by a first line extending through and away from said top edge and a second line extending through said first side edge, with said outside angle being between about 100° and 126°.

7. A nose splint, as claimed in claim 6, wherein:
   said top surface has a width and said bottom surface has a width, with said bottom surface width being greater than said top surface width.

8. A nose splint, comprising:
   an outer layer that is malleable for conforming to a shape of an outer contour of a nose;
   a support assembly that is attached to said outer layer and which includes:
      an inner layer having a mid-portion and an inner surface; and
      a pad member located at said mid-portion of said inner layer, said pad member having a top surface, a bottom surface, a first side, a second side, a first end and a second end, said top surface having a top edge adjacent said first end and said first side having a first side edge adjacent to said first end, with a first line being definable through said top edge and a second line being definable through an intersection of said first side edge, with an outside angle being defined by an intersection of said first and second lines and said outside angle being in the range of about 100° and 126°.

9. A nose splint, as claimed in claim 8, wherein:
   said bottom surface is greater in width than said top surface.

10. A nose splint, as claimed in claim 8, wherein:
    said inner layer includes at least one of the following: a foam material and separable fabric materials including hooks and loops.

11. A nose splint, as claimed in claim 8, wherein:
    said pad member is separate from and non-integral with said inner layer, said pad member being attached to said inner layer after the shape of said pad member is fixed.

12. A nose splint, comprising:
    an outer layer that is malleable for conforming to an outer shape of a nose; and
    a support assembly attached to said outer layer and which includes:
       an inner layer attached to said outer layer and having an inner surface with a mid-portion;
       a pad member located at said mid-portion of said inner layer and with a discontinuity being defined at a juncture between said inner surface and said pad member, said pad member having a top surface and a bottom surface, said top surface being joined to said inner surface and with said top surface being less in width than said bottom surface, wherein said pad member also has a first side with a first side edge and said top surface has a top edge, a first line is definable as extending through and being parallel to said top edge and a second line is definable as extending through and being parallel to said first side edge, an outside angle being defined by an intersection of said first and second lines and said angle being in the range of about 100° to 126°.

13. A nose splint, as claimed in claim 12, wherein:
    said pad member is separate from but attached to said inner surface of said inner layer after the shape of said outer layer is provided.

14. A nose splint, as claimed in claim 12, wherein:

said inner layer includes at least one of the following: a foam material and separable fabric materials having hooks and loops.

15. A nose splint, comprising:

an outer layer that is malleable for conforming to an outer shape of a nose; and a support assembly attached to said outer layer and which includes:

an inner layer attached to said outer layer and having an inner surface with a mid-portion;

a pad member located at said mid-portion of said inner layer and with a discontinuity being defined at a juncture between said inner surface and said pad member, said pad member having a top surface and a bottom surface, said top surface being joined to said inner surface and with said top surface being less in width than said bottom surface, said width of said top surface being in the range of about 3.0 mm–4.4 mm.

16. A nose splint, as claimed in claim 15, wherein:

said width of said bottom surface is in the range of about 5.0 mm–7.75 mm.

17. A nose splint, comprising:

an outer layer that is malleable for conforming to an outer shape of a nose; and a support assembly attached to said outer layer and which includes:

an inner layer attached to said outer layer and having an inner surface with a mid-portion;

a pad member located at said mid-portion of said inner layer and with a discontinuity being defined at a juncture between said inner surface and said pad member, said pad member having a top surface and a bottom surface, said top surface being joined to said inner surface and with said top surface being less in width then said bottom surface, said bottom surface having a radius in the range of about 11–17 mm.

\* \* \* \* \*